United States Patent
Poser et al.

(10) Patent No.: US 10,551,280 B2
(45) Date of Patent: Feb. 4, 2020

(54) ARRANGEMENT AND METHOD FOR INSPECTING AN OBJECT, IN PARTICULAR A BUILDING

(71) Applicant: TECTUS DREAMLAB PTE LTD, Singapore (SG)

(72) Inventors: Marcel Poser, Oberuzwil (CH); Malcolm Lim, Buffalo Grove, IL (US)

(73) Assignee: TECTUS DREAMLAB PTE LTD, Singapore (SG)

( * ) Notice: Subject to any disclaimer, the term of this patent is extended or adjusted under 35 U.S.C. 154(b) by 324 days.

(21) Appl. No.: 15/033,219

(22) PCT Filed: Oct. 30, 2013

(86) PCT No.: PCT/EP2013/072705
§ 371 (c)(1),
(2) Date: Apr. 29, 2016

(87) PCT Pub. No.: WO2015/062646
PCT Pub. Date: May 7, 2015

(65) Prior Publication Data
US 2016/0282230 A1     Sep. 29, 2016

(51) Int. Cl.
*G01M 99/00*     (2011.01)
(52) U.S. Cl.
CPC .................... *G01M 99/00* (2013.01)
(58) Field of Classification Search
None
See application file for complete search history.

(56) References Cited

U.S. PATENT DOCUMENTS 6,725,097 B1   4/2004  Basile et al.
7,289,918 B2  10/2007  Nagase
(Continued)

FOREIGN PATENT DOCUMENTS

EP   1 213 560 A1   6/2002
EP   2 472 226 A2   7/2012
(Continued)

OTHER PUBLICATIONS

Japanese Office Action issued in corresponding Japanese Patent Application dated Jun. 27, 2017 [To Follow].
(Continued)

*Primary Examiner* — Alexander G Ghyka
(74) *Attorney, Agent, or Firm* — David & Bujold PLLC; Michael J. Bujold (57) ABSTRACT

An arrangement (1) for inspecting an object (2) comprising a mobile measuring unit (13) for determining a measured value associated with the object (2). The measuring unit (13) has an interface for interchanging data with further units (12, 14-17). The arrangement also comprises a base unit (3; 12) in which data records (13) can be stored and displayed. A detection mechanism (14) is provided for detecting a measurement position (32), at which the measured value is determined, and/or a measurement time at which the measured value is determined. The measured value determined by the measuring unit (13) can be transmitted, together with measurement position and/or measurement time, as a data record to the base unit (3; 12). The mobile measuring unit (13) determines measured values for an internal structure and/or an internal state of components (8), in particular inaccessible components, of the object (2) in a non-destructive manner.

18 Claims, 6 Drawing Sheets

(56) References Cited

U.S. PATENT DOCUMENTS

| | | | |
|---|---|---|---|
| 2004/0028258 A1* | 2/2004 | Naimark | G06K 9/4609 382/103 |
| 2004/0153270 A1 | 8/2004 | Yamashita et al. | |
| 2007/0106462 A1* | 5/2007 | Blain | G05D 1/10 701/518 |
| 2007/0219645 A1* | 9/2007 | Thomas | G05B 15/02 700/29 |
| 2008/0247635 A1* | 10/2008 | Davis | G06T 19/00 382/152 |
| 2008/0247636 A1* | 10/2008 | Davis | G06T 19/00 382/152 |
| 2012/0023435 A1* | 1/2012 | Kneppers | G06Q 50/16 715/780 |
| 2013/0061696 A1 | 3/2013 | Cabuz | |
| 2014/0168423 A1 | 6/2014 | Koga | |

FOREIGN PATENT DOCUMENTS

| | | |
|---|---|---|
| JP | H09-177321 A | 7/1997 |
| JP | H11327628 A | 11/1999 |
| JP | 2001289827 A | 10/2001 |
| JP | 2002323401 A | 11/2002 |
| JP | 200330469 A | 1/2003 |
| JP | 2005-050098 A | 2/2005 |
| JP | 2007305147 A | 11/2007 |
| JP | 2012032217 A | 2/2012 |
| JP | 2013149042 A | 8/2013 |
| WO | 94/01766 A1 | 1/1994 |
| WO | 00/73739 A1 | 12/2000 |
| WO | 2013030929 A1 | 3/2013 |

OTHER PUBLICATIONS

International Search Report Corresponding to PCT/EP2013/072705 dated Jun. 2, 2014.

Japanese Office Action issued in corresponding Japanese Patent Application No. 2016-550944 dated Jun. 27, 2017.

Japanese Office Action issued in corresponding Japanese Patent Application No. 2016-550944 dated Apr. 26, 2018.

Japanese Office Action issued in corresponding Japanese Patent Application No. 2016-550944 dated Feb. 12, 2019.

* cited by examiner

ARRANGEMENT AND METHOD FOR INSPECTING AN OBJECT, IN PARTICULAR A BUILDING

The invention relates to an arrangement and a method for inspecting an object, in particular a construction, according to the preambles of the independent claims.

BACKGROUND OF THE INVENTION

Constructions require regular and detailed inspections by qualified inspection specialists, in order to detect a state of the construction. This correspondingly also applies to many other objects. The inspections can provide information about whether e.g. the structural integrity of the object is ensured. Constructions—in particular buildings, repositories, bridges, towers, tunnels, roads and protective equipment—have to be regularly checked in order to ensure sufficient fitness for use and load bearing safety. Checking is effected during production, during use, repurposing and possible retreat of the constructions.

Such inspections sometimes require taking account of a multiplicity of data and parameters. By way of example, during the inspection of constructions, it is necessary to take account of material characteristics of components, operating parameters, specifications and recommendations from possible standards and guidelines and e.g. particular requirements made of a component in the context of the entire construction. There is therefore a need to provide an inspection system which enables the highest possible integration of a multiplicity of data and makes the latter available to the inspection specialist in a clear manner.

The inspections of a construction typically comprise a comprehensive examination of the construction in which inspection-relevant situations such as e.g. defects and/or disturbances of the construction or of individual components are visually identified and detected. Hereinafter, without restricting the generality for inspection-relevant situations reference is made by way of example to defects. An inspection specialist analyzes these defects in a further step and, on the basis thereof, derives a diagnosis e.g. of a type of the defect or of a topology of the defect. The diagnosis is taken as a basis for making a decision e.g. about further inspection steps and/or measures for eliminating the defects. This entails the risk that defects and the possible effects thereof on the construction will be overlooked and/or incorrectly assessed by the inspection specialist.

Registering the defects usually comprises entering the defects on a diagram such as e.g. a construction plan of a construction during the inspection by the inspection specialist. Subsequently, the registered defects are generally detected electronically and e.g. entered into a database or included in a CAD-based construction plan of the construction or a model of the construction created for example with the aid of a 3D scanner known per se. This procedure firstly has the disadvantage that the detection of the defects is solely dependent on the perception and care of the inspection specialist. However, the detection of the defects forms the basis of all further measures and should therefore have an increased redundancy with which e.g. the risk of erroneous entries or undiscovered defects can be reduced. Secondly, transferring the diagrammatically detected defects into an electronic data acquisition entails the risk of transfer errors e.g. as a result of an erroneous inputting of numerical values. Moreover, in this way it is not subsequently possible to track at what point in the inspection an error occurred. Furthermore, the repeated transfer of data is inefficient and labor-intensive. By way of example, it is not possible to track whether a defect was actually detected by the inspection specialist or was lost e.g. only at a later time e.g. during the transfer of the data.

An integrated system which attempts to overcome at least some of the existing disadvantages is described in U.S. Pat. No. 6,725,097 B1. This system allows visually recognizable defects to be input into a mobile input device that the inspection specialist carries during the inspection. The defects can e.g. be classified on the basis of their visible structure in accordance with a predefined selection and be drawn on plans of the construction. In this case, the defect can be drawn manually in a construction plan e.g. by means of a graphical input program or a photograph can be taken on site. The input device can additionally comprise programmed algorithms for analyzing the defects that have been input.

While this system has improved interactivity and data integration, the detection of the inspection data is effected only by the inspection specialist, as in earlier systems, and thus has no or only low redundancy. Consequently, the advantageously automated analysis of the defects is also based solely on the detected defects, i.e. the perception and care of the inspection specialist during their detection. The system offers no protection against defects that are overlooked during detection, nor does it allow subsequent ascertainment of whether a defect was overlooked or did not occur until after the inspection.

Therefore, a problem addressed by the invention is that of overcoming the disadvantages of the prior art. In particular, a problem addressed by the invention is that of providing a diversely applicable arrangement and a diversely applicable method for inspecting an object, in particular a construction, which enables a reliable detection of the actual state and also of structural deficiencies. Moreover, the arrangement and the method are intended to be convenient to operate and to implement and are intended to ensure a high degree of safety. Moreover, the arrangement and the method are intended to ensure that at a later time it is possible to track at what point on the object, in particular on the construction, an inspection-relevant situation was detected.

SUMMARY OF THE INVENTION

These problems are solved by an arrangement and a method having the features of the independent claims.

The latter relate, in a first aspect, to an arrangement for inspecting an object, in particular a construction, comprising a mobile measuring unit for determining a measurement value assigned to the object, wherein the measuring unit has an interface for data exchange with further units of the arrangement, in particular a base unit. Furthermore, the arrangement comprises an, in particular mobile, base unit, in which data sets communicated by the measuring unit are storable and preferably visually representable and which has an interface for data exchange with further units of the arrangement, in particular at least the mobile measuring unit. Preferably, the base unit additionally has an interface for data exchange with a proprietary or public network. The arrangement also comprises a detection means for detecting a measurement position at which the measurement value is determined, and/or for detecting a measurement time at which the measurement value is determined. In this case, a measurement value determined by the measuring unit is communicatable at least together with a measurement position detected by the detection means, preferably automatically, as a data set to the base unit. In this case, the mobile measuring unit is designed for nondestructively determining measurement values concerning an internal structure and/or an internal state of, in particular inaccessible, elements of the object, in particular components of the construction. The determination of the measurement value can be carried out for example by a user on sits who operates the measuring unit. In this case, user on site denotes a user present during the inspection at the object, such as e.g. an inspection specialist entrusted with the inspection. Alternatively, the measuring unit can also be designed in such a way that it is remotely controllable, for example via the base unit.

Here and hereinafter, a construction is understood to mean a structure built by human beings which is in static contact with the foundation. The construction can be a building, for example, which serves for instance for residence of human beings, accommodation of animals, cultivation of plants or storage of items or operation of machines. The construction can also be a traffic construction, such as for instance a bridge, a road, a tunnel or a gallery. Alternatively, the construction can also be a supply and/or disposal construction, such as for instance a well, a water pipe and/or sewer, a sewage treatment plant, a dike, an impounding dam, a masonry dam, a weir, a chimney, a tower (such as for instance a wind tower or a transmission tower), a transmission mast or an overhead power line pylon. Furthermore, the construction can be a protective structure, such as for instance a nuclear power plant or a protective well, a protective dam, a system for breaking up avalanches, a road screen or a shelter. The construction can also be a weir installation and/or fortification installation, such as for instance a fortification or a weir tower. Moreover, the term "construction" also encompasses mines and opencast mines and temporary constructions, such as for instance temporary structures, tents, trade fair pavilions, auxiliary structures, container structures and depositories.

In addition to constructions, the term "object" used here and hereinafter for example also encompasses in particular movable articles, such as for instance, devices, machines, vehicles, aircraft, items of furniture, works of art (wherein for example the authenticity thereof can be ascertained with the arrangement according to the invention and/or the method according to the invention), but also living objects, such as plants, animals or human beings.

Here and hereinafter, an "internal structure" and an "internal state" are understood to mean a structure and respectively a state of the object which are not able to be recognized purely visually, as would be possible for example by a user with the naked eye or with the aid of a camera. The terms "internal structure" and "internal state" thus encompass, on the one hand, structures and states within the object. However, they also encompass structures and states which are present at a surface of the object that is indeed visible per se to the user, or in the region of such a surface, but which are not able to be recognized purely visually. By way of example, in the context of the invention, an elasticity of the object in the region of a visible surface is also regarded as an internal state since such an elasticity is not able to be recognized purely visually.

The base unit and/or the measuring unit preferably comprise means for storing, for processing, for inputting and outputting and for receiving and communicating data. A storage unit and a computing unit can be present for storing and processing the data. In particular, the base unit can be designed in such a way that the data structures, programs, data sets (original and/or derived data sets) and/or instructions also described in detail further below are storable on the base unit.

The means for inputting can comprise e.g. a touch-sensitive area and/or a keypad and/or a microphone. Via a touch-sensitive area, drawings, for example, can be registered by a user. A keypad allows the user to input text including numerals. Voice input can be effected via a microphone. These data thus input can then be communicated together with the associated measurement value determined by the measuring unit and an associated measurement position and/or measurement time detected by the detection means as a data set to the base unit and optionally be stored and/or processed further there. In this way, a type of logbook can arise which can be used to record what user carried out what measurement at what time and at what location, how and for what reason.

The means for outputting can comprise a printer, for example, via which a measurement log, for example, can be output. However, the means for outputting are preferably designed in such a way that object-specific, in particular construction-specific, data or data structures are visually representable. A combined means for inputting and outputting can be provided e.g. by a touch-sensitive screen.

As visual representation, an, in particular three-dimensional, virtual model of the object to be inspected can be visually representable to the user on site on the base unit and/or the measuring unit. Given suitable means for inputting, the user on site can interact with the virtual model, if appropriate, such as e.g. choose views or mark measurement positions. Instructions for the user on site can likewise be represented, such as for example measurement instructions for the user on site which indicate e.g. a measurement position and/or a measurement time and/or a type of measurement.

In some embodiments, it may suffice if the arrangement contains only a single base unit. The outlay in terms of apparatus can be reduced as a result. Particularly for the inspection of relatively large and/or relatively complex objects, however, the arrangement can also contain a plurality of base units. The latter can then each have interfaces for data exchange among one another.

The measuring unit is advantageously designed in such a way that it is portable for the user on site; in particular, it can be correspondingly dimensioned and have a corresponding weight for this purpose. Alternatively, the measuring unit can have been positioned or can be positioned for example in or on an in particular remotely controllable vehicle.

The base unit is preferably designed as a mobile unit which a user on site e.g. can carry into the object, in particular into a construction, or can position outside the object, in particular outside a construction, e.g. in or on a vehicle. The base unit is advantageously designed in such a way that it is portable for the user; in particular, it can be correspondingly dimensioned and have a corresponding weight for this purpose. Preferably, the base unit is implemented e.g. in a carrying case or in the manner of a laptop or tablet computer. The base unit preferably has a protective housing that affords protection against mechanical damage e.g. in the hazardous environment of a construction site. Alternatively, the base unit can have been positioned or can be positioned for example in or on an in particular remotely controllable vehicle. In principle, however, the base unit can also be arranged e.g. as a maintenance or inspection terminal fixedly on the object, in particular on the construction.

The base unit can have an interface for data exchange with a, wire-based or wireless, proprietary or public external network. In this way, the base unit can be linked to a localized (e.g. server unit) or delocalized (so-called "cloud") network service unit. Correspondingly, in particular in real time, data can be communicated to the network service unit or be obtained from the latter. By way of example, the Internet (public) or a mobile radio network (proprietary) can be employed as external networks.

It is also possible and lies within the scope of the invention for the base unit itself to be designed as a server or to contain a server. Data exchange between the interface of the measuring unit and the server can then be effected via a proprietary or public network. In this embodiment, the data sets communicated by the measuring unit are storable in said server, and the server contains an interface for data exchange with further units of the arrangement.

In other embodiments, it is also conceivable for the measuring unit and the base unit jointly to form an integrated device and to be enclosed for example in a common housing.

The mobile measuring unit can be designed as a portable handheld device that can be positioned at the measurement position e.g. by the user on site. The measuring unit comprises at least one measuring device for determining internal structures or an internal state of the components. By way of example, the state of reinforcements in reinforced concrete elements can be determined by the measurement of induced eddy currents and/or conductivity measurements. The mobile measuring unit has an interface for data exchange with further units of the arrangement, in particular the base unit. The measuring unit can be linked to the base unit or further units of the arrangement in this way e.g. via a wireless local area network (WLAN). Wire-based links are likewise conceivable, of course. In this way, the determined measurement data of the measuring unit and, if appropriate, position data of the detection means can be communicated e.g. automatically to the base unit. The communication can be effected directly upon detection of the measurement values or at predefined or adapted time intervals. For this purpose, the measurement data can be buffer-storable in the measuring unit. It goes without saying that a manual initiation of the transfer may also be necessary, or a transfer is effected only after the measuring unit has been linked to the base unit, e.g. by the connection of a cable.

In this case, "measurement position" can denote a position which is specified with respect to an e.g. global coordinate system such as GPS coordinates. The measurement position can likewise also be specified with respect to a local reference system such as e.g. of the object itself or of a positioning system designed specifically for the inspection of the object. A determination of the measurement position can in particular also be effected or specified visually, e.g. by means of photographic or film-based detection of the measurement process or of the measurement position in relation to further features of the object with a known position, as will be described in even more detail further below.

The detection means can be designed for manually inputting the measurement position e.g. as numerical sequences. The measurement position can likewise be implemented e.g. by means of a manual marking of the measurement position on a virtual model of the object that is represented on the measuring unit. For this purpose, the detection means can be integrated into the measuring unit e.g. as a keypad and/or as a touch-sensitive screen. It goes without saying that the detection means can also comprise a receiver for signals of a satellite-based (e.g. GPS) or ground-based global positioning system, said receiver being implemented e.g. in the measuring unit. The receiver can likewise be designed e.g. for receiving signals of one or a plurality of radio beacons that are set up on site at the object for establishing a coordinate system and allow e.g. a triangulation of the measurement position. A determination of the measurement position can be initiated automatically upon the detection of the measurement value.

The required functionalities of the individual units or means can be implemented via hardware and/or software depending on the requirement. Interactions of the user on site may also be necessary depending on the requirement.

On account of the separate base unit, e.g. a further user on site, but not necessarily at the measurement position, can monitor the detection of the measurement values. In particular, at the base unit it can be ensured that the detected measurement values were implemented at the correct measurement positions, as provided e.g. in an inspection plan. In particular, it is also possible to check directly on site at the object whether the measurement positions and measurement values were entered e.g. at the correct position in a plan of the object stored in the base unit, in particular in a construction plan of a construction stored in the base unit. If there are indications of an erroneous or incomplete detection, the inspection specialist, at the base unit, can influence the course of the inspection and e.g. arrange for a renewed or additional performance of a measurement. The further user on site at the base unit has the advantage here that the inspection can be monitored in convenient surroundings and with access to diverse additional information that said further user can obtain via the network, for example.

By virtue of the fact that a measurement is effected nondestructively according to the invention, an overview of the internal state or an internal structure e.g. of a concrete component can be obtained rapidly even at locations at which, for static or construction engineering reasons (e.g. lack of space, poorly accessible locations), it is not possible to take core samples for a laboratory analysis. In this way, the arrangement allows a direct measurement of e.g. internal structural defects and/or disturbances and not just the assumption thereof on account of externally recognizable defects. In particular, externally invisible defects can be determined independently of the perception of the user on site. In this way, the arrangement can be used particularly diversely, e.g. also for acceptance of a newly produced object. By way of example, a measuring unit of the present arrangement that is designed as a reinforcement testing device can be used to test whether the reinforcements in a concrete element of a construction correspond to the structural stipulations. Such structural deficiencies are not able to be recognized visually.

On account of the base unit, these determined data directly on site at the object can e.g. be integrated into a data model or a data structure and be visualized. Consequently, directly on site it can become recognizable that further measurements and/or visual inspections must be performed e.g. on account of a determined internal defect in a vicinity of the measurement position. By virtue of the measuring unit, in particular also a plurality of, preferably different, measuring units, being linkable to the base unit, the data determined by the different measuring units can be acquired centrally by the base unit. In this case, the base unit allows e.g. an integration of the different data determined into an existing data structure that reproduces an internal state of the measured elements of the object, in particular of the measured components of the construction. The data structure can be storable in the base unit. In particular, said data structure can also comprise plans and further information concerning the object, in particular construction plans and further information concerning the construction, such that overall a comprehensive virtual model of the object can be provided which reliably reproduces a current state of the object. All linked measuring units can thus access an updated central data structure without excessive synchronization outlay.

In this case, the data structure can also comprise measurement data of earlier inspections, such that a history of the elements or of the object, in particular of the components or of the construction, is detectable. The data structure supplemented with the data concerning the internal structure of the elements, in particular of the components, can be visualized or output by the base unit e.g. as a virtual model or in some other way. It goes without saying that alternatively or additionally e.g. the data structure and/or the visual representation can be stored or generated on a server to which the base unit is linked (see below). It likewise goes without saying that the base unit if necessary is also designed only for collecting and forwarding data sets obtained by the arrangement according to the invention. The data structure and e.g. a visual conditioning of the data can be implemented on the server in this case.

Preferably, the mobile measuring unit is designed for carrying out at least one or a plurality of the following measurements:

ultrasonic measurement,
radiography (in particular penetrating radar measurement),
eddy current measurement,
electrical resistance measurement,
potential field measurement,
rebound measurement,
acoustic resonance analysis (in particular in accordance with Guideline US06 of the DGZfP (German Society for Nondestructive Testing), for example using the Erudite system, obtainable from CNS Farnell Limited, Hertfordshire, UK),
inductive reinforcement locating (in particular in accordance with DGZfP leaflet B02, for example using Profoscope PS 250, obtainable from Proceq SA, Schwerzenbach, Switzerland),
capacitive reinforcement locating (in particular in accordance with DGZfP leaflet B02, for example using PS 38 Multidetector, obtainable from Hilti Corporation, Adliswil, Switzerland),
ground penetrating radar (GPR) (in particular in accordance with DGZfP leaflet B10),
strain gauge testing,
tightness testing (in particular in accordance with one or more of the standards EN 1779, EN 13184, EN 13185 and EN 1593),
radiographic testing (in particular in accordance with one or more of the standards EN 444, EN 13068 and EN 16016, in particular radiographic testing with the aid of X-ray radiation),
penetrant testing (in particular in accordance with the standard EN 571-1),
capacitive moisture measurement (in particular in accordance with the standard EN 13183-3, for example using one of the moisture measuring devices from Tramex Ltd., Dublin, Ireland),
resistive moisture measurement (in particular in accordance with the standard EN 13183-3, for example using one of the moisture measuring devices from Tramex Ltd., Dublin, Ireland),
impact echo method (in particular in accordance with DGZfP leaflet B11, for example using one of the devices from James Instruments Inc., Chicago, USA),
infrared thermography (in particular in accordance with one or more of the standards DIN 54190, DIN 54192 and EN 13187, using thermal emission, passively or by active preheating),
conductivity testing (for example using a Wenner probe, such as for instance Resipod, obtainable from Proceq SA, Schwerzenbach, Switzerland),
magnetic-inductive method (in particular in accordance with the standard ISO 2178),
magnetic powder testing (in particular in accordance with the standard ISO 9334),
potential field measurement (in particular in accordance with DGZfP leaflet B03, for example using the Canin system, obtainable from Proceq SA, Schwerzenbach, Switzerland),
rebound hammer method (in particular in accordance with the standard EN 12504-2, for example using the Schmidt hammer, obtainable from Proceq SA, Schwerzenbach, Switzerland),
acoustic emission analysis (in particular in accordance with the standard EN 12504-2),
shearography (laser speckle shearing interferometry), in particular for mobile inspection for the nondestructive testing of composite components),
leakage field measurement (in particular for detecting fatigue and/or stress cracks in prestressed concrete constructions),
ultrasonic testing (in particular in accordance with the standard EN 583, and/or the DGZfP leaflet B04, for example using the Pundit system, obtainable from Proceg SA, Schwerzenbach, Switzerland),
vibration testing/oscillation analysis (in particular in accordance with at least one of the standards ISO 13373 and DIN 45669),
eddy current testing (in particular in accordance with the standard ISO 15549, for example for crack testing, for layer thickness measurement and/or for determining material properties),
time domain reflectometry (in particular in accordance with the standard DIN 19745, for example using the TRIME system, obtainable from IMKO GmbH, Ettlingen, Germany),
laser induced plasma spectroscopy (LIPS),
metal hardness measurement (in particular for measuring the Leeb hardness, the Rockwell hardness, the Brinell hardness and/or the Vickers hardness),
magnetic resonance imaging (MRI, as known from medical applications, for example),
X-ray fluorescence measurement, (for example using the device FISCHERSCOPE® X-RAY XDV®-SD, obtainable from Helmut Fischer AG, Hünenberg, Switzerland),
microresistance method (in particular in accordance with the standard DIN EN 14571:2005, for example using the device SR-SCOPE® RMP30-S, obtainable from Helmut Fischer AG, Hünenberg, Switzerland),
beta backscatter method (in particular in accordance with at least one of the standards DIN EN ISO 3543, ASTM B567 and BS 5411, for example using a FISCHERSCOPE® MMS®, obtainable from Helmut Fischer AG, Hünenberg, Switzerland),
coulometric measurement (in particular in accordance with the standard DIN EN ISO 2177:2004-08, for example using the device COULOSCOPE®, obtainable from Helmut Fischer AG, Hünenberg, Switzerland), linear polarization method (in particular for estimating a corrosion current in reinforced concrete).

An ultrasonic measurement is based in principle on a pulse velocity measurement of an ultrasonic pulse. By means of a waveform analysis, conclusions can be drawn about the properties of the construction material. In this way, it is possible both to check the homogeneity of the construction material and to demonstrate defects. The pulse or the velocity is related to the density and elasticity of the construction material to be tested, which enables e.g. a statement regarding quality and compressive strength.

In a penetrating radar measurement, the internal structure of the component is measured by the reflection of electromagnetic radiation at defects. In this case, generally very short electromagnetic pulses having a length of from a few picoseconds to a few nanoseconds are emitted into the interior of the component and the reflection is captured. In this case, the propagation of the electromagnetic waves in the interior is dependent on the structures situated in the component that bring about reflection, scattering, diffraction and transmission of the signal radiated in. The time of flight, the phase and the amplitude of the reflected signal are usually recorded.

In the eddy current measurement, an alternating magnetic field is generated e.g. by a coil, and induces eddy currents in a conductive construction material. During the measurement, the eddy current density as a result of the magnetic field generated by the eddy current is detected by means of a sensor, which usually also comprises the excitation coil. The measured parameters generally comprise the amplitude and the phase shift with respect to the excitation signal. They are usually measured by the use of a second coil in the sensor. Occasionally, other magnetic field sensors, such as GMR sensors (giant magnetroresistance) or so-called SQUIDs (superconducting quantum interference device), are also used. Eddy current testing exploits the effect that most impurities and instances of damage in an electrically conductive material also have a different electrical conductivity or a different permeability than the actual material.

The measurement of the electrical resistivity provides information about the state of a component, such as e.g. a reinforced concrete element. The resistivity is closely related to the probability of corrosion and the corrosion rate. Likewise, the resistivity can be directly correlated with a chloride diffusion rate. During the measurement, generally a first pair of electrodes is brought into contact with the construction material. A voltage is applied between the electrodes. The potential difference between a further pair of electrodes is subsequently measured. The resistivity can be calculated therefrom and from the arrangement of the electrodes.

The potential field measurement can involve ascertaining whether a corrosion activity is present e.g. at a reinforcement in the reinforced concrete. In this case, an electrochemical potential between steel and concrete, to put it more precisely between the steel and a half-cell (e.g. copper/copper sulfate reference electrode) placed onto the concrete, is measured at certain intervals over the entire concrete area. Anodic and cathodic regions can be determined from the potential field thus determined. In the case of regions having an anodic potential, the steel corrodes or is at least particularly at risk of corrosion.

In the rebound measurement, basically a striking pin is accelerated in the measuring unit, said striking pin striking the construction material and rebounding. The harder the construction material, the further the pin rebounds. The rebound distance is e.g. indicated on a scale or detected automatically and is a measure of the rebound energy. A strength of the construction material can be read from this. With a series of measurements, an internal structure of the construction material can be determined on the basis of different compressive strengths.

It goes without saying that the arrangement can comprise a plurality of measuring units based on different measurement principles. Likewise, individual measuring units can also comprise measuring devices for a plurality of measurement methods. It goes without saying that it is also possible to employ measurement units which are suitable on other nondestructive measurement principles for measuring internal structures or an internal state of the component. However, the present selection of measurement methods has proved to be economically implementable and worthwhile in daily use.

In one preferred embodiment of the arrangement, the detection means comprises an in particular mobile capture unit, which is designed and positioned or positionable before the determination of the measurement value at a measurement position in such a way that the determination of the measurement value, in particular by the user on site, by means of the mobile measuring unit is capturable photographically and/or on film by the capture device. In this case, the capture unit is preferably designed to be mobile and as a separate and freely positionable unit. It is advantageously designed in such a way that it is portable for a user on site; in particular, it can be correspondingly dimensioned and have a corresponding weight for this purpose. In one advantageous embodiment, the capture unit is arranged on a helmet worn by a user on site; this allows at least substantially the capture of the field of view of the user, in particular while said user carries out a measurement with the aid of the measuring unit. The capture unit is preferably linked or linkable to the base unit via an interface, wherein the interface can be wire-based or wireless. If appropriate, the capture unit can also be linked to the measuring unit, wherein this linking, too, can be wire-based or wireless.

In this case, the capture unit allows a region of the object in which measurement values are determined e.g. at different measurement positions to be detected simultaneously with an in particular fixed field of view. The field of view preferably encompasses at least the mobile measuring unit and/or the user on site during the determination of the measurement value and surroundings of the measurement position. For this purpose, the capture unit can be positioned by the user on site in advance of the determination of the measurement values. By virtue of the fact that the capture unit records the determination of the measurement values e.g. photographically and/or on film, at a later time it is possible to demonstrate without any doubt which measurement values were determined at which locations of the object and, if appropriate, by which user on site they were determined.

The capture unit can comprise a buffer store (buffer memory) that stores captured shots during a limited period of time (for example 5 seconds) in accordance with a FIFO principle (first-in first-out). In this way, at any measurement time it is possible to store captured shots before, during and after the determination of the measurement values. The capture time can be initiated e.g. automatically by the performance of the measurement by the measuring unit. In this case the capture unit, e.g. the field of view thereof, can serve e.g. as a reference system for the determination of the measurement positions. The capture unit can likewise comprise e.g. radio beacons for position determination of the measuring units via radiowaves.

Preferably, at least one field of view which encompasses at least the user during the determination of the measurement value and surroundings of the measurement position is detectable with the capture unit. In this way, size relationships and a position of the user on site when carrying out the measurements are recognizable on the captured shots. For this purpose, the capture unit can comprise e.g. a wide-angle or panoramic camera. It goes without saying that, given a suitable design, a conventional camera can also be used.

The arrangement can comprise a triangulation system. In this case, a triangulation system denotes a system with which, on the basis of e.g. ground- and/or satellite-based signals, a position of the measuring unit, in particular a measurement position, is determinable during the measurement process. By way of example, a radio beacon or an antenna system on site at the object can be employed as a ground-based triangulation system. By way of example, a global positioning system such as the freely available GPS can be employed as a satellite-based triangulation system.

The arrangement, in particular the mobile measuring unit, can alternatively or additionally contain a displacement capture system, with the aid of which the movement of the mobile measuring unit is determinable. The displacement capture system can comprise a wheel, for example, which is rolled along a surface of the inspected object during the measurement. The movement of the mobile measuring unit can be deduced from the rotation of the wheel. For this purpose, the wheel can contain a magnet, the movement of which is ascertained inductively.

It goes without saying that the detection means in variants can also comprise a coordinate grid which is projected by means of a laser, for example, and with which a measurement position is determinable.

The arrangement can furthermore comprise a marking unit, with which the measurement position is markable on the object. In this way, the measurement positions can be visibly marked directly on the object for a later reference. By way of example, it is conceivable to apply the marking by means of a separate marking gun (e.g. in the manner of a paintball gun). Preferably, however, the marking unit is integrated into the measuring unit, such that the measurement position is markable during the determination of the measurement value.

The marking can comprise a color marking or, e.g. for the case where the region to be marked ought not to be visually impaired, a fluorescent marking, which becomes visible only in a specific light. The marking unit can function in the manner of an inkjet printer. In this way, not only is it possible to mark the measurement position, but it is also possible to record additional indications such as e.g. type and time of the measurement. The marking data can be communicated identically to the base unit, such that a data structure assigned to the object and the object itself comprise the same marking indications.

The arrangement can furthermore comprise a macro capture unit, with which direct surroundings of the measurement position are capturable photographically and/or on film. In this case, the macro capture unit should be differentiated from the abovementioned capture unit to the effect that the macro capture unit is provided for capturing a detail view of the measurement position. The macrograph serves to document the state of the component at the measurement position in a detailed manner. For this purpose, the macro capture unit can comprise a camera suitable for macrographs and/or a microscope camera. Preferably, the macro capture unit is integrated into the measuring unit, such that the direct surroundings of the measurement position are capturable during the determination of the measurement value. It is ensured in this way that the correct measurement position is captured by the macro capture unit in the state during or shortly before or shortly after the measurement.

Likewise alternatively or additionally, the arrangement can comprise an inertial navigation system. With an inertial navigation system, proceeding from a known starting point e.g. on the object, a current position is determinable by integration of data from acceleration sensors. Such a system generally has a total of six kinematic degrees of freedom, of which three are translational and three are rotational, which are oriented toward likewise three unit vectors situated orthogonally with respect to one another. With this sensor assembly, the body coordinate system can be determined in real time and compared via a kinematic transformation with a fixed, previously known, spatial coordinate system, which enables an application as a navigation system.

In a first variant, the inertial navigation system can be integrated into the capture unit of the detection means. The direction in which the captured shots are captured by the capture unit can thereby be determined in a particularly simple manner. In a second variant, however, the inertial navigation system can also be integrated into a macro capture unit. The direction in which the captured shots are captured by the macro capture unit can thereby be determined in a particularly simple manner. This is advantageous particularly if the macro capture unit is integrated in the mobile measuring unit and the direct surroundings of the measurement position are captured.

The arrangement can comprise for repeatedly determining a measurement value at a selected measurement position, a monitoring unit fitted to the object temporarily or permanently, said monitoring unit having an interface for data exchange with further units of the arrangement, in particular the base unit and/or a server described in even greater detail further below. The monitoring unit can be designed for example for carrying out at least one or a plurality of the following measurements:

ultrasonic measurement,
radiography,
eddy current measurement,
electrical resistance measurement,
potential field measurement,
rebound measurement,
acoustic resonance analysis,
inductive reinforcement locating,
capacitive reinforcement locating,
ground penetrating radar,
strain gauge testing,
tightness testing,
radiographic testing,
penetrant testing,
resistive moisture measurement,
impact echo method,
infrared thermography,
conductivity testing,
magnetic-inductive method,
magnetic powder testing,
potential field measurement,
rebound hammer method,
acoustic emission analysis,
shearography,
leakage field measurement,
ultrasonic testing,
vibration testing/oscillation analysis,
eddy current testing,
time domain reflectometry, laser induced plasma spectroscopy,
metal hardness measurement,
magnetic resonance imaging,
X-ray fluorescence measurement,
microresistance method,
beta backscatter method,
coulometric measurement,
linear polarization method,
moisture measurement,
temperature measurement,
radiation measurement (for example measurement of electromagnetic and/or radioactive radiation),
acceleration measurement,
linear displacement capture measurement,
rotation measurement,
measurement of optical fibers contained in the object.

With regard to the measurements, the monitoring unit can be designed largely analogously to a measuring unit as described above. In the case of the monitoring unit, however, in principle it is also possible to apply other measurement principles such as e.g. of a visual inspection, in particular of a purely visual inspection, of an exterior of the component. However, the monitoring unit need not be mobile, and input and output means can also be dispensed with, in principle. The monitoring unit can comprise an interface for linking to an external network, such that measurement data are communicatable e.g. directly to a network service unit without a detour via the base unit.

The arrangement, in particular the measuring unit, can furthermore contain a recording device, which detects at least one acceleration value and/or a moisture value and/or a temperature value and/or a specific radiation value preferably together with the measurement time and/or the measurement position if at least one predefined threshold value of one of these values was exceeded. Such a recording device can recognize possible damage to the measuring unit which might influence the measurement values. The recording device can be arranged in the measuring unit or in the base unit. By way of example, a high acceleration of the measuring unit may indicate that the measuring unit was inadvertently dropped by the user and therefore possibly no longer yields reliable measurement results. The recording device can thus have the function of a "black box".

In addition to the measurement value determined by the measuring unit and the measurement position and/or measurement time detected by the detection means, the data set that is communicatable to the base unit and storable there can furthermore contain at least one additional measurement value, such as, for example, a strain value and/or a moisture value and/or a temperature value and/or a specific radiation value and/or an acceleration value and/or a measurement value that was determined by a monitoring unit as described above.

The interface of the base unit is advantageously designed for linking to a public or proprietary network, wherein the arrangement comprises a server, to which the base unit is linked or linkable for data exchange via the public or proprietary external network, wherein the server is accessible to an authorized user via a, preferably public, network. In this case, the server can be a specific implementation of the abovementioned network service unit with which services can be provided or implemented via the network.

In this case, the server is designed to receive and store data from the base unit. The data can likewise be conditionable by the server. A server has the advantage over a base unit that the data determined can be made available independently of the base unit also to third parties who are authorized only for access to the server but not to the arrangement according to the invention for inspection. Such authorized users may be e.g. customers of a provider of the arrangement described in the present case or members of a construction acceptance authority, who can have first-hand access to the inspection data in this way. In particular, the authorized users can also directly track the inspection of the object in a virtual way and if appropriate influence said inspection, for example by instructions also described in detail further below.

Preferably, the server comprises at least one stored data structure which is assigned to the object to be inspected. In this case, the server is designed to supplement the data structure with data communicated by the base unit and to provide the supplemented data structure to the authorized user, in particular in real time. In this case, the data structure forms a uniform format for data from different sources. On the one hand, external data concerning the object, in particular external data concerning the construction such as e.g. constructions plans of the construction, historical inspection data and/or technical specifications or standard data concerning the elements, in particular the components, can be included in the data structure. On the other hand, the data structure can be supplemented by the server with data or data sets of the base unit comprising measurement values of the measuring units or, if appropriate, of the monitoring units. Likewise, e.g. captured shots of the in particular mobile capture unit and/or of the macro capture unit can be integratable into the data structure. The server thus forms a so-called data warehouse in which data concerning the object from different sources can be combined (information integration) and provided e.g. in a uniform format. This improves convenience when accessing the data of the object.

The data structure is preferably constituted in such a way that from the data structure a virtually accessible three-dimensional model of the object to be inspected, in particular of the construction to be inspected, can be provided by the server to the authorized user and/or the user on site. In this context, "accessible" denotes that the authorized user can move largely freely in the virtual model e.g. as a so-called avatar. In this case, a user on site can simultaneously be represented as an avatar in the same model, such that e.g. interactions between the authorized user and the user on site are possible via the server, which can result in a kind of team meeting "on site". Given a corresponding design, the virtual model can be representable e.g. on the base unit and/or on the measuring unit and/or on a head-up display, in particular a head-up display of spectacles, which can be worn by the user on site or the authorized user.

The data structure and the virtual model based thereon is preferably augmentable by the server continuously with the data communicated by the base unit concerning internal structures and/or an internal state of the components of the measuring units. In this way it is ensured that the model provided by the server is up to date and the inspection is monitorable in real time e.g. by the authorized user.

In said virtual model, it is possible to superimpose a data structure and/or original and/or derived data sets and/or measurement instructions and/or capture instructions and/or instructions for determining at least one additional measurement value in real time, such that a "virtual augmented reality" model arises. By way of example, the measurement positions can be marked in the virtual model and be implemented as a reference (similar to a reference (hyperlink) of an Internet page), such that the desired information concerning an internal state and/or an internal structure can be retrieved given corresponding action by the user. In the virtual model, the internal structures can be represented visibly e.g. through semitransparent walls, wherein additional information such as setpoint values or computationally simulated values e.g. of corrosion of a reinforcement can be inserted. In this case, critical measurement values concerning internal defects or defective regions can be highlighted in color, for example.

Preferably, the server comprises a library of programs with which data sets of the data structure that are selected in a targeted manner by the authorized user are conditionable and/or retrievable. In this way, firstly, e.g. three-dimensional views and, secondly, object reports, in particular construction reports, can be generated from the data structure. In this case, the programs in the library allow the corresponding relevant data firstly to be extracted from the data structure and secondly to be conditioned in the desired form.

Advantageously, an instruction can be communicated by an authorized user via the server. By way of example, a measurement instruction can be communicatable to the base unit, and if appropriate from the latter, to the monitoring unit and/or to the mobile measuring unit and/or to the user on site. Particularly if the measuring unit is remotely controllable, the measurement instruction is preferably communicated directly to the measuring unit. The measurement instruction can comprise e.g. a measurement position and/or a measurement time and/or a type of the measurement which is intended to be carried out by the user on site. The communication of one or a plurality of measurement instructions can be effected in real time. Alternatively or additionally, however, one or a plurality of measurement instructions can also be compiled beforehand and then be made available as a collection to the user on site. The measurement instruction or a plurality of measurement instructions can be compiled e.g. before the inspection on the server in the form of an inspection plan for the user on site. If appropriate, the desired measurement positions can be represented in the virtual model. Preferably, however, the measurement instruction is communicated to the user on site in real time, such that the inspection can be directly influenced e.g. by the authorized user. The authorized user need not be on site at the object for this purpose.

Alternatively or additionally, it is possible to communicate to the detection means an instruction for determining at least one additional measurement value, for example a strain value and/or a moisture value and/or a temperature value and/or a specific radiation value and/or an acceleration value determined by an acceleration sensor. The communication of the additional measurement value is preferably effected in real time.

Likewise alternatively or additionally, a capture instruction can be communicated to the in particular mobile capture unit and/or to the macro capture unit, preferably in real time.

The measurement instruction and/or the instruction for determining at least one additional measurement value and/or the capture instruction can contain indications concerning the measurement position at which the measurement or capture is intended to be effected. In this case, it is conceivable that the measurement or capture is effected automatically if the predefined measurement position is reached. The arrangement, in particular the measuring unit or the macro capture unit, can have been or be correspondingly programmed for this purpose so that the measurement or capture is then effected automatically.

The server can be designed as a localized server unit e.g. at a provider of the arrangement for construction inspection described in the present case. Preferably, however, the server is provided as an information technology infrastructure that is dynamically adaptable to a demand, in particular as a cloud-based server. In this way, the capacities of the server can be expanded as necessary without any problems. By way of example, the server can be correspondingly extended in the case of a particularly comprehensive data structure on account of a high complexity of the object or in the case of special requirements on the part of an authorized user with regard to the quality of the visual representation. If the demand fails, unnecessary resources can be excluded cost-effectively.

The delocalized server structure of a cloud-based server additionally ensures that the data available on the server or the services provided by the server remain available, even if individual regions of the server fail. The range of the services offered in the context of cloud computing in this case encompasses the entire spectrum of information technology and includes inter alia infrastructure such as e.g. computing power, storage space, platforms and software.

A further aspect of the invention relates to a method for inspecting an object, in particular a construction, in particular for implementation using an arrangement as described in the present case. The method comprises the following steps:

nondestructively determining a measurement value concerning an internal structure and/or an internal state of, in particular inaccessible, elements of the object, in particular components of the construction, by a mobile measuring unit, detecting a measurement position at which the measurement value is determined, and/or a measurement time at which the measurement value is determined, by a detection means, in particular automatically, communicating the measurement value determined by the measuring unit at least together with the measurement position detected by the detection means as a data set via a data interface to a base unit, storing the data set in the base unit.

The measuring unit can be operated by a user on site. However, it is also conceivable and lies within the scope of the invention for the measuring unit to be remotely controllable and for operation by a user not to be needed.

The advantages of this method are evident directly from the arrangement for inspecting an object, in particular a construction, as described in the present case.

The method can additionally comprise the following steps:

communicating a data set from the base unit to a server, in particular comprising measurement values concerning an internal structure and/or an internal state of, in particular inaccessible, components, preferably via a public or proprietary network, wherein the server comprises at least one stored data structure assigned to the object to be inspected, supplementing the data structure with the data set communicated by the base unit, providing, in particular in real time, the data structure, in particular on the server, in particular as a virtually accessible three-dimensional model of the object to be inspected, for an authorized user and/or a user on site.

As an alternative to the embodiment mentioned above, the data structure can also be provided on the base unit or on a head-up display.

When nondestructively/determining a measurement value concerning an internal structure and/or an internal state of the component, use is preferably made of at least one of the measuring methods already mentioned above. Likewise, the method can comprise positioning a detection means, designed as an in particular mobile capture unit, at a measurement position, wherein the in particular mobile capture unit is positioned before the determination of the measurement value in such a way that the determination of the measurement value by the user on site is capturable photographically and/or on film by the capture device. In this case, the in particular mobile capture unit preferably detects a field of view that encompasses at least the user during the determination of the measurement value and surroundings of the measurement position.

In order to train persons for the use of the arrangement according to the invention and/or of the method according to the invention, it may be advantageous for the server to be made accessible to these persons. The authorization can be restricted temporally and/or to specific rights. By way of example, it can be restricted to a read access, such that said persons have for example no right to supplement and/or modify the data structure stored by the server. However, the persons can be authorized to receive data from the server in order, for example, to represent the object to be inspected as a virtually accessible three-dimensional model.

Further modifications of the method are evident from the arrangement for inspecting an object as described in the present case.

BRIEF DESCRIPTION OF THE DRAWINGS

The invention is explained in greater detail with reference to drawings of exemplary embodiments. In the figures, schematically.

DETAILED DESCRIPTION OF THE INVENTION

Figure 1:
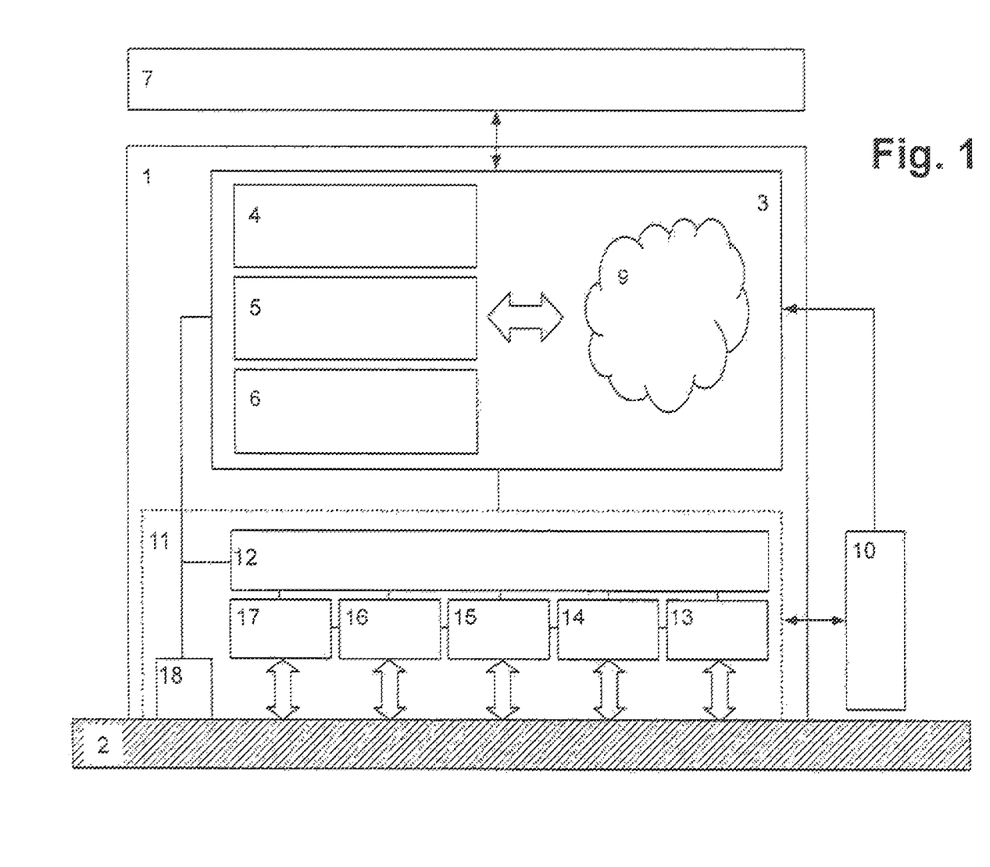
FIG. 1: shows a block diagram of an arrangement according to the invention comprising a server.

FIG. 1 shows a block diagram of an arrangement 1 according to the invention for inspecting an object designed as a construction 2, said arrangement comprising a server 3. FIG. 1 illustrates the functional units as separate blocks which, in specific implementations, can be embodied separately or can be combined in part in one device. In this case, the server 3 can be designed as a localized server unit e.g. at a provider of the arrangement 1. The server 3 can likewise be embodied as a delocalized, cloud-based server 3.

The server 3 comprises a library of different applications 4 with which data or data structures stored on the server 3 can be e.g. analyzed, processed and/or managed. According to the situation, applications 4 can be provided e.g. by authorized users 7 themselves, in order to enable e.g. individualized data processing. In this case, it is possible to access a program library 5 of the server 3 that has e.g. standardized program routines for two- and/or three-dimensional outputting of data, text outputting and/or other data conditioning.

The server 3 comprises a database 6 in which data can be stored. The data are preferably stored in a predefined or dynamically adaptable, standardized data structure which enables uniform access to a wide variety of types of data. In particular, by way of example, image files, sound files and data files or individual data points can be combined in the uniform data structure. In this case, the data structure can be assigned e.g. to a construction 2 that has been inspected or is to be inspected. In this way, for each construction 2 inspected by means of the arrangement 1, it is possible to provide a comprehensive collection of information in a simply and diversely accessible data format. The data structure preferably has at least data of three-dimensional construction plans of the assigned construction 2. Said data can be augmented e.g. with historical data of earlier inspections. Likewise, e.g. the processed construction materials of the individual components can be stored.

It goes without saying that the server 3 has e.g. computing units and interfaces for data exchange, in order to provide the required functionalities. The server 3 is additionally designed, or the program library 5 comprises corresponding program routines, for mapping the data or data structure stored in the database into a visually representable, three-dimensional virtual model 9 of the construction 2. The conversion into the visual representation can be effected e.g. by a client-side application on a personal computer of the authorized user 7. Likewise, the visual representation can also be implemented on the server 3 and be transferred as image or film files to the computer of the authorized user.

The virtual model 9 is preferably implemented as an accessible and interactive virtual model 9. The authorized user 7 or a user on site 10 who is occupied with the inspection of the construction 2 can thus "enter" the virtual model 9. In this case, the user can be present purely as an observer in the virtual model 9 or be represented by a so-called avatar. For this purpose, the model 9 can have input possibilities via which the authorized user 7 and/or the user on site 10 or the avatar(s) thereof can interact with the model 9. By way of example, distinguished locations at the virtual model 9 can be embodied as activatable references (similar to the references—hyperlinks—of an Internet page) that refer to further data. In this case, e.g. construction data such as the type of concrete used, planned number of reinforcements in the concrete or historical data of earlier inspections can be retrieved by interaction.

Preferably, data can also be input via the model 9. In particular, e.g. distinguished locations at which e.g. measurements are intended to be carried out by the user on site 10 can be markable in the model 9 by the authorized user or the avatar thereof. The stored data and/or the data structure can thus be altered, in particular supplemented, by interaction with the model 9. Further possibilities of such an accessible three-dimensional virtual model 9 of the construction 2 to be inspected are afforded directly, in particular in association with a test arrangement 11, as is described below.

The test arrangement 11 comprises at least one base unit 12 and one or a plurality of measuring units 13. Alongside the measuring unit 13, the test arrangement 11 can comprise a detection means 14 for detecting a measurement position and/or a measurement time at which a measurement is carried out by the measuring unit 13. Furthermore, a marking unit 15 can be present, with which the measurement position of a measurement can be marked or the construction 2. In addition, a macro capture unit 16 can be present, which can create a visual macrograph of the measurement position with the direct surroundings thereof. Capture is preferably effected shortly before, during and/or shortly after the measurement by the measuring unit 13.

The detection means 14 can comprise a capture unit that can visually detect a section of the construction 2 in which measurements are carried out together with the user on site 10. Such a capture unit can also, e.g. as a further detection means, be designed as a separate capture unit 7. By way of example, the detection means 14 can be integrated into the measuring unit 13 and comprise a triangulation system, while the separate capture unit 17 serves for additional visual detection of the measurement position. The capture unit 17 is described in greater detail e.g. with reference to FIG. 4.

The measuring unit 13, the detection means 14, the marking unit 15, the macro capture unit 16 and if necessary the separate capture unit 17 are linked to the base unit 12 for data exchange preferably via a network. In this case, the data exchange can be effected automatically and e.g. directly in the case of changes in the data structure. It goes without saying that data during the inspection can also be stored in the individual units 13 to 17 and not be transferred to the base unit 12 until at a later time. The network can be of wire-based or wireless design, wherein in each case a proprietary or public network can be used.

The base unit 12 is linked to the server 3 via a further or the same network. The data of the units 13 to 17 are thus transferrable to the server 3 via the base unit 12. The server 3 supplements the data structure assigned to the construction 2 with the communicated data. The supplementations can be accepted into the data structure e.g. in real time. The virtual model 9 generated from the data structure can likewise be provided with the supplementations in real time. In this way, a user 7 or 10 can be informed in real time e.g. about a measurement that has been performed. It goes without saying that data can be transferred e.g. to the measuring unit 13 e.g. also from the server 3 via the base unit 12. Such data can comprise e.g. a measurement instruction generated by an authorized user 7, said measurement instruction being displayed to the user on site 10 on a display of the base unit 12 and/or the measuring unit 13.

One exemplary sequence is as follows:

The user on site 10 carries out the measurement owing to the measurement instruction, wherein said user is detected e.g. by the capture unit 17. The data thus obtained—such as e.g. measurement values of the measuring unit 13, measurement positions detected by the detection means 14, captured overview shots of the capture unit 17 with the user on site 10 when carrying out the measurement and/or macrographs of the macro capture unit 16—can be communicated to the server 3. The latter supplements the data structure and, if appropriate, generates a supplemented virtual model 9. The authorized user 7 can thus access the supplemented data and check them e.g. for quality and/or completeness.

The test arrangement 11 can also comprise at least one monitoring unit 18 arranged e.g. fixedly on the construction 2. The monitoring unit 18 is linked to the server 3 and/or the base unit 12. The monitoring unit 18 can, like the measuring unit 13, capture measurement values of components of the construction 2. In contrast to the measuring unit 13, however, the monitoring unit 18 in this exemplary embodiment is designed as a stationary unit for continuously communicating measurement values.

Figure 2:
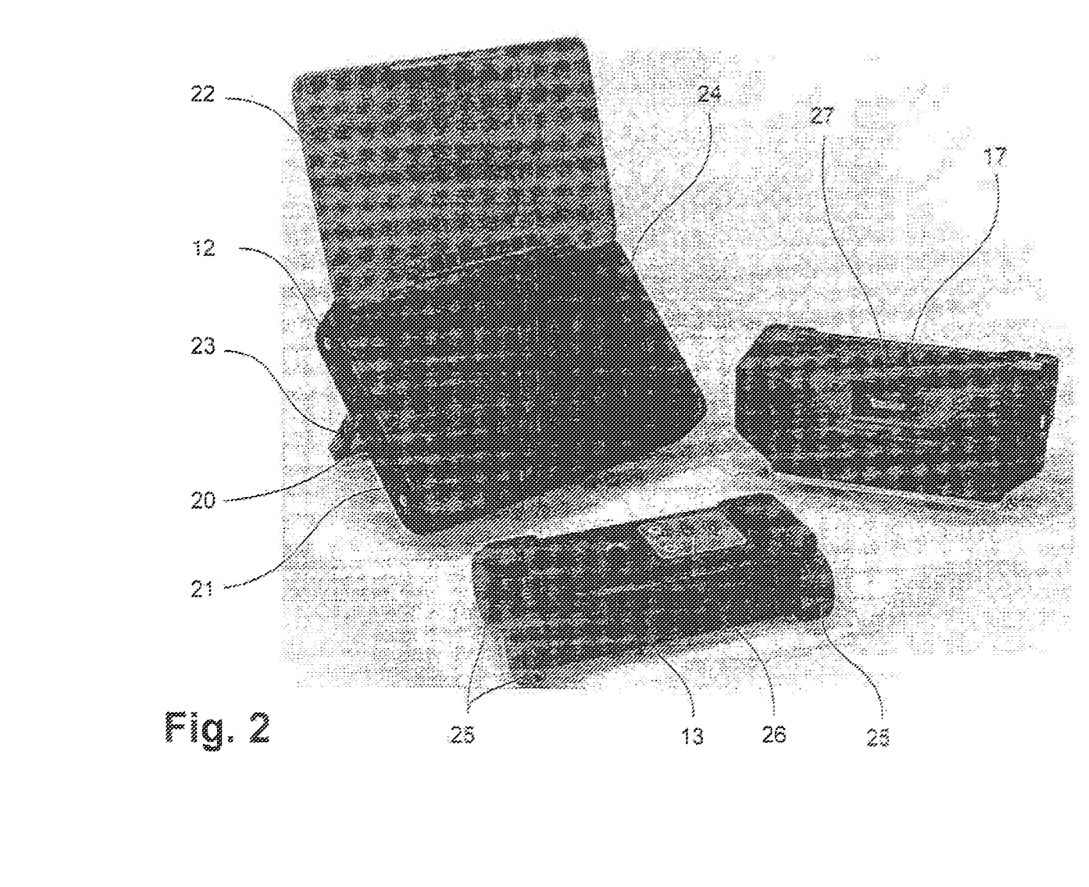
FIG. 2: shows exemplary embodiments of a base unit and of a detection means designed as a capture unit, and of a measuring unit of an arrangement according to the invention.

FIG. 2 shows exemplary embodiments of the base unit 12 and of a detection means designed as a separate capture unit 17, and of a measuring unit 13. The measuring unit 13 is described below by way of example with reference to a reinforcement testing device based on an eddy current technology.

The base unit 12 has a screen 20, which in the present case is designed as touch-sensitive for inputting data. The base unit 12 has a protective housing 21 with a cover 22, with which the screen 20 can be protected. In addition, means 23 for positioning the base unit 12 in a desired position can be implemented on the protective housing 21. The base unit 12 can be designed substantially like a robust laptop or tablet computer, such as is also employed for use in the field. The base unit 12 can additionally have a keypad 24, with which inputs can be made.

The measuring unit 13 has a measuring device (not discernible here) designed for carrying out the measurement method respectively employed. In the present case, these are for example coils for carrying out an eddy-current-based reinforcement test in e.g. reinforced concrete. The measuring unit 13 comprises a likewise touch-sensitive screen 26 for representing and inputting data.

Furthermore, the measuring unit 13 contains four wheels 25, which can be rolled along a surface of the inspected object during the measurement. One of the wheels 25 contains a magnet (not discernible here), the movement of which can be ascertained inductively. The trajectory along which the measuring unit 13 is guided over the surface of the object can be determined particularly precisely in this way.

Figure 4:
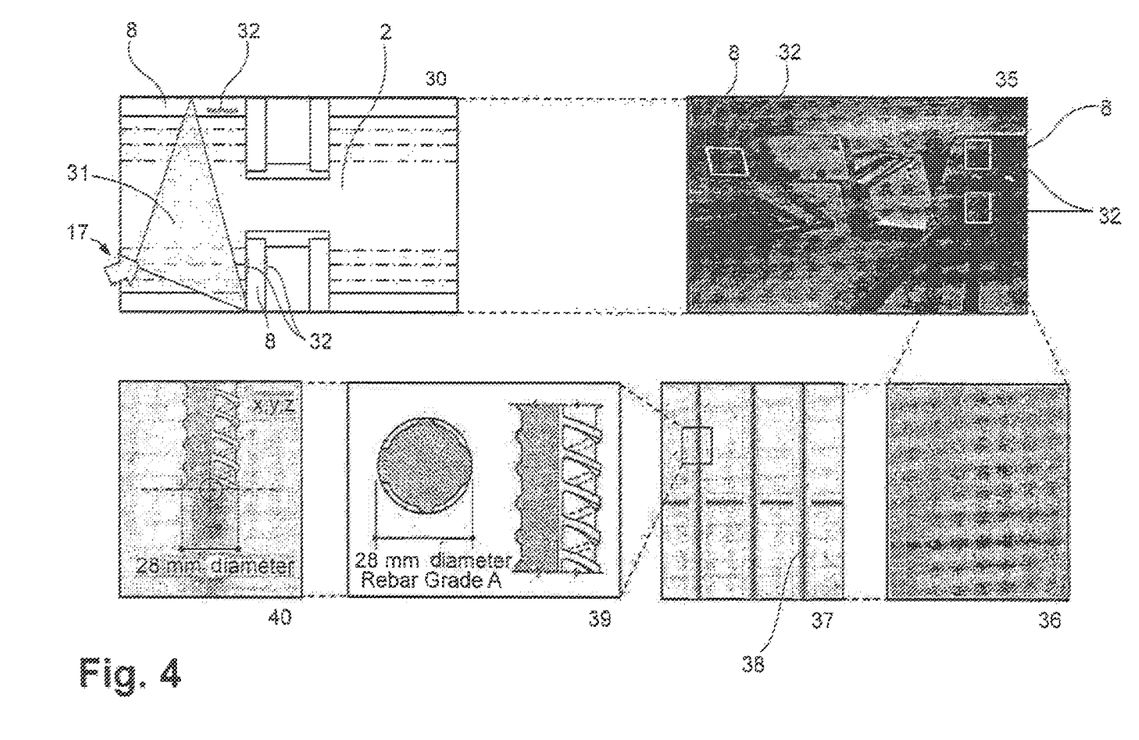
FIG. 4: shows various views such as are generatable e.g. by a program routine from a data structure assigned to the construction or from a virtual model.

The capture unit 17 has a camera 27 having a comparatively large field of view, such that a region of the construction 2 is detectable in an overview view 35 (see e.g. FIG. 4). If necessary, the camera 27 can comprise a wide-angle lens or a fisheye. The camera 27 can also be designed as a panoramic camera.

Figure 3:
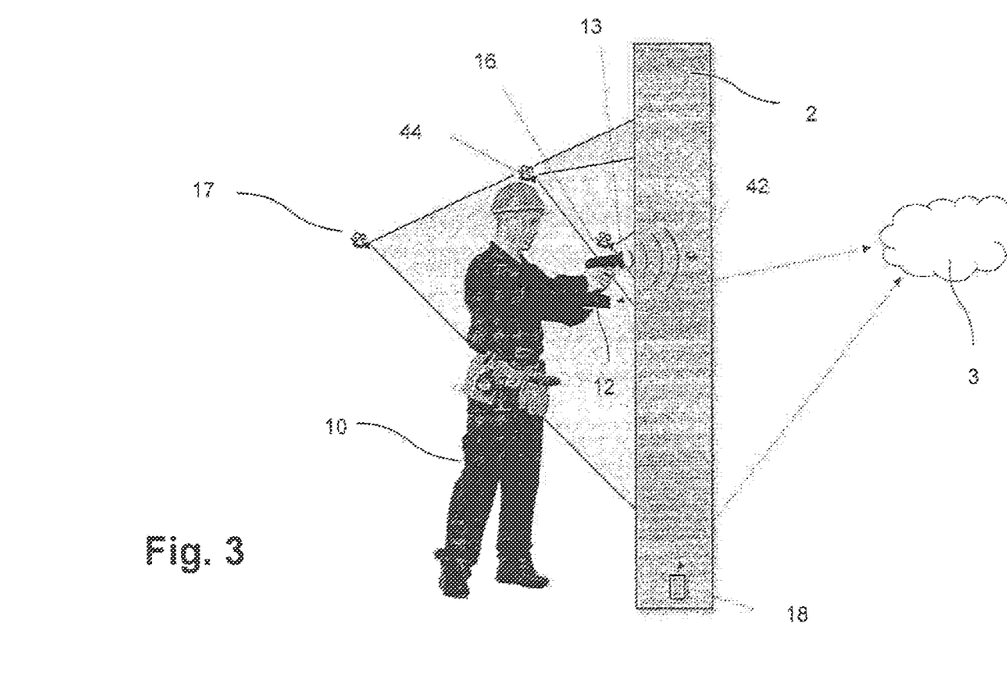
FIG. 3: shows an illustration of a measurement by a user on site.

FIG. 3 schematically illustrates how a user on site 10 can perform a measurement. Said user can determine a measurement value of the object 2 with the aid of a mobile measuring unit 13. Said measurement value is influenced by a defect 42 and can thus provide information about the presence of the defect 42. The measuring unit 13 is connected to a base unit 12 via an interface for data exchange, in which base unit data sets communicated by the measuring unit 13 are storable. The base unit 12 furthermore has an interface for data exchange with a proprietary or public network 3. Alternatively, the interface of the base unit 12 can also be designed for direct data exchange with a server. There is arranged on the measuring unit 13 a macro capture unit in the form of a camera 16, with the aid of which the exact measurement position can be recorded. A further camera 44, arranged on the helmet of the user on site 10, substantially detects the field of view of the user on site 10. The field of view of a further camera 17 detects the user on site 10 during the measurement. A monitoring unit 18 is fixed to the object 2, which monitoring unit can be designed for example as a moisture sensor or as a temperature sensor. The monitoring unit 18 also has an interface for data exchange with the network 3.

FIG. 4 shows a view 30 such as is generatable from the data structure assigned to the construction 2 or from the virtual model 9 e.g. by a program routine of the program library 5. The view 30 shows a two-dimensional plan view of a section of the construction 2. A desired position and a desired viewing direction and viewing angle 31 of the capture unit 17 are displayed in the view 30. In addition, measurement positions 32 are marked on different components 8 of the construction 2 in the field of view of the capture unit 17. The view 30 can thus be regarded as a measurement instruction for the user on site 10. It goes without saying that view 30 can also show a situation of this region after a measurement has been effected, wherein the marked measurement positions 32 in this case can be designed e.g. as activatable references via which e.g. the measurement values of the measurements can be accessed.

View 35 in FIG. 4 shows the field of view of the capture unit 17 with the inserted measurement positions 32 of the components 8. In this case, the view 35 can be understood e.g. as a three-dimensional view of the already supplemented virtual model 9. The view 35 can likewise be regarded as a three-dimensional view of a measurement instruction to the user on site 10 which can be represented e.g. on the base unit 12 or the measuring unit 13. In this case, the user on site 10 is informed about where said user has to carry out the measurements. In this case, a color of the marked measurement positions 32 can indicate e.g. the desired type of measurement.

View 36 shows a macrograph of the direct surroundings of one of the measurement positions 32, such as is captured by the macro capture unit 16. The macrograph can be called up e.g. by mouse click or other interaction with the corresponding measurement position 32 in the virtual model 9.

View 37 shows a visual representation of determined measurement values. The measuring unit 13 has determined e.g. the positions and a state of reinforcements 33 in the component 8 by means of one or a plurality of measurements. The measurement values were processed into a visual representation of the raw data by the base unit 12 or the server 3. The visual representation can be called up e.g. by mouse click or other interaction on the corresponding measurement position 32 in the virtual model 9.

View 39 snows detailed information concerning an excerpt from the view 37. The represented information may comprise e.g. additional information from a library concerning the construction materials used or may have been generated computationally e.g. from the measurement values of the measuring unit 13.

View 40, finally, shows a superimposed view in accordance with views 36, 37 and 39, such as can be represented in the virtual model 9. In addition, the exact spatial coordinates of the measurement position as determined, e.g. by the detection means 14 can be inserted (X, Y, Z).

Figure 5:
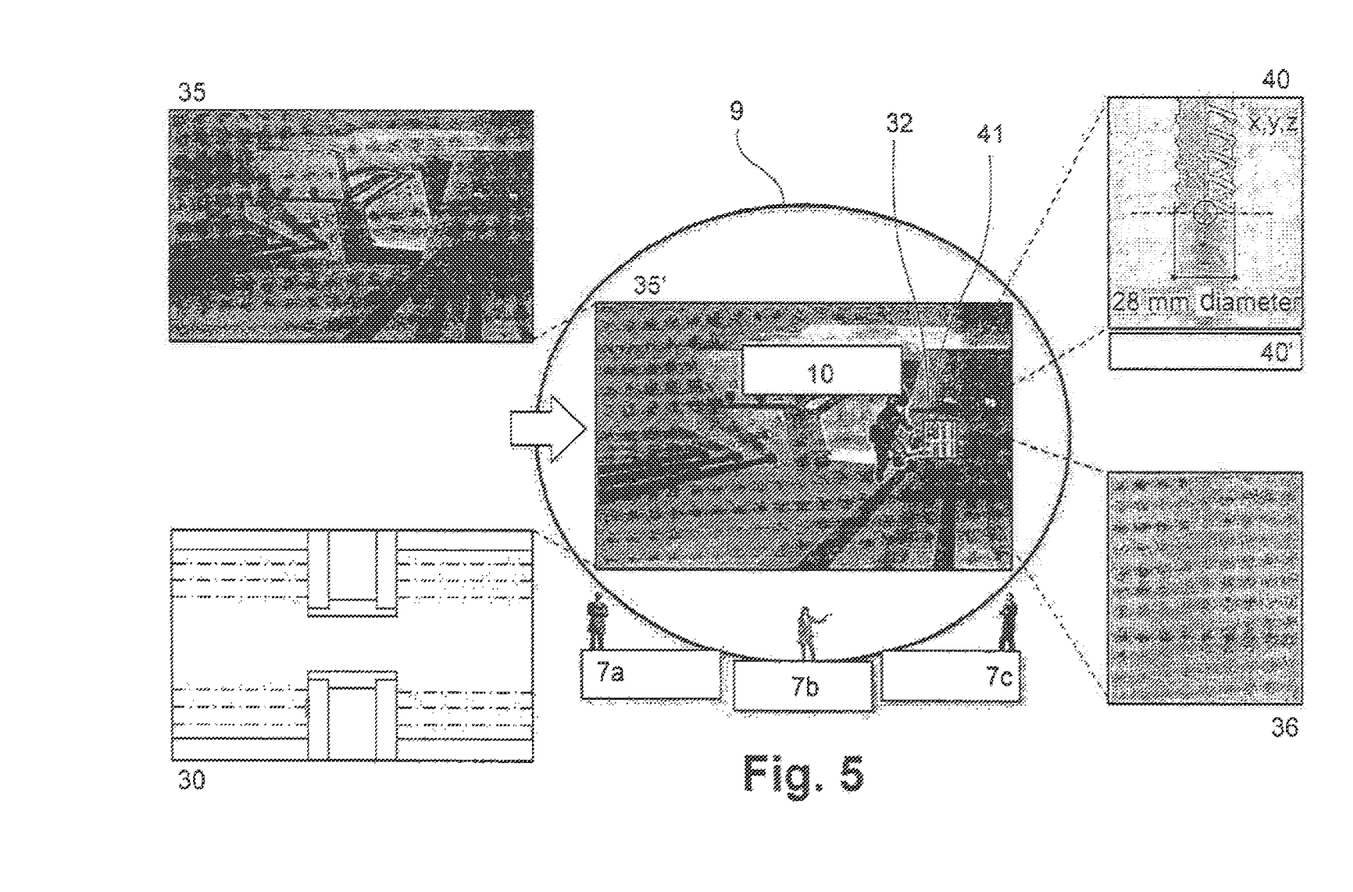
FIG. 5: shows a block diagram with various views of how a supplemented data structure can be represented as a supplemented virtual model after an inspection has been carried out.

FIG. 5 shows schematic views of how the supplemented virtual model 9 can be represented after an inspection has been carried out by the user on site 10. The determined measurement values and further data were included in the supplemented model 9 (arrow). A three-dimensional representation 35' of the supplemented model 9 can be retrieved by authorized users 7 on the server 3. The authorized users 7 may be in this case e.g. a service specialist 7*a*, an owner 7*b* of the construction 2 or an employee 7*c* of the inspection company.

The view 35', corresponding to the field of view of the capture unit 17 in the view 35, shows the user on site 10 when carrying out the measurement. The measurement position 32 is marked and can be implemented as an interactive reference 41. Via the reference 41, a multiplicity of items of information linked thereto can be retrievable. By way of example, the view 36 of the macro capture unit 16 can be retrieved. The composite view 40 can likewise be called up. It goes without saying that the measurement position 32 of the view 35' can be represented e.g. directly as a composite view 40.

It goes without saying that all the views can be supplemented with text fields 40' in which e.g. details concerning the measurement such as the time or type of the measurement can be displayed. The result of an analysis of the measurement values can likewise be displayed, such as e.g. "corrosion 10%". It goes without saying that the supplemented data such as e.g. the viewing angle 31 of the capture unit 17 in the view 35 and/or the two-dimensional representation in accordance with the view 30 can also be gathered from the model 9. Further data of the data structure can likewise be accessed, which e.g. give information about the standards to be complied with for the component 8 or concern earlier inspection data.

Figure 6:
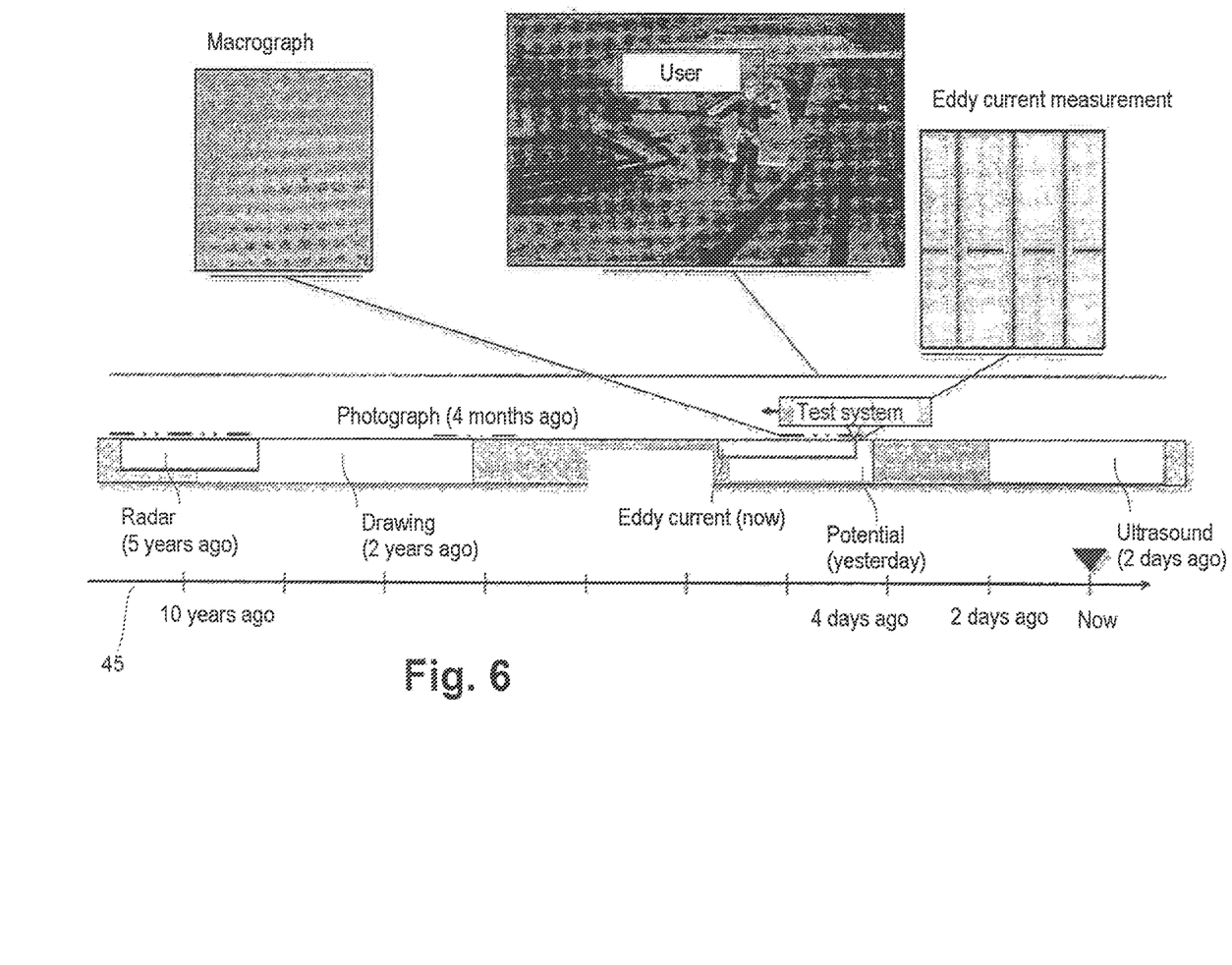
FIG. 6: shows a visual reproduction represented on a screen with a timeline.

FIG. 6 illustrates a visual reproduction represented on a screen and containing a timeline 45. The history of a multiplicity of measurements is represented along the timeline 45. The individual measurements are marked and implemented as references, such that, given corresponding action by the user, the desired information concerning an internal state and/or an internal structure can be retrieved, as is illustrated in FIG. 6 by way of example for an eddy current measurement carried out on the same day.

The invention claimed is:

1. An arrangement for inspecting an object, the arrangement comprising:
   a mobile measuring unit comprising a measuring device for determining a measurement value assigned to the object, and the measuring unit has an interface for data exchange with further units of the arrangement,
   a base unit, in which data sets communicated by the measuring unit are storable and which has an interface for data exchange with the further units of the arrangement,
   a detection means for detecting at least one of:
      a measurement position at which the measurement value is determined, or
      a measurement time at which the measurement value is determined,
   wherein the measuring unit is designed to communicate a measurement value determined by the measuring unit at least together with a measurement position and/or measurement time detected by the detection means as a data set to the base unit,
   and the measuring device is designed for non-destructively determining measurement values concerning an internal structure and/or an internal state of elements of the object,
   the interface of the base unit is designed for linking to a public or proprietary external network,
   and the arrangement comprises a server to which the base unit is linked or linkable for data exchange, via the public or proprietary network, and the server is accessible by an authorized user via a network,
   the server comprises at least one stored data structure which is assigned to the object to be inspected,
   and the server is designed to supplement the data structure with data communicated by the base unit and to provide the supplemented data structure to the authorized user and/or a user on the site,
   the server is designed to provide a virtually accessible three-dimensional model of the object to be inspected to the authorized user and/or the user on site,
   and the data structure and the virtual model based thereon are created and are then continuously augmentable by the server with the data communicated by the base unit concerning of an internal structure and/or an internal state of elements of the object, wherein the object is a construction or a movable article.

2. The arrangement as claimed in claim 1, wherein the elements are components of the construction.

3. The arrangement as claimed in claim 1, wherein the detection means comprises a capture unit, which is designed and positionable before the determination of the measurement value at a measurement position in such a way that the determination of the measurement value by the mobile measuring unit is capturable photographically and/or on film by the capture device.

4. The arrangement as claimed in claim 3, wherein the mobile measuring unit is designed for determining a measurement value assigned to the object by a user on site and the determination of the measurement value is performed by the user on site.

5. The arrangement as claimed in claim 3, wherein at least one field of view which encompasses at least the mobile measuring unit and/or a user on site during the determination of the measurement value and surroundings of the measurement position is detectable with the capture unit.

6. The arrangement as claimed in claim 1, wherein a marking unit is present with which the measurement position is markable on the object.

7. The arrangement as claimed in claim 1, wherein a macro capture unit is present, with which direct surroundings of the measurement position are capturable photographically and/or on film.

8. The arrangement as claimed in claim 1, wherein the server is designed to provide the virtually accessible three-dimensional model in real time.

9. The arrangement as claimed in claim 1, wherein an instruction is communicatable by the authorized user via the server.

10. The arrangement as claimed in claim 9, wherein the instruction contains indications concerning the measurement position at which the measurement or capture is intended to be effected.

11. The arrangement as claimed in claim 10, wherein the arrangement is programmed in such a way that the measurement or the capture is automatically effected when the predefined measurement position is reached.

12. A method for inspecting an object, the method comprising the following steps:
providing a mobile measuring unit comprising a measurement device,
providing detection means,
wherein the mobile measuring unit non-destructively determines a measurement value concerning an internal structure and/or an internal state of components of the object, and the detection means detects a measurement position at which the measurement value is determined, and/or a measurement time at which the measurement value is determined,
communicating the measurement value determined by the measuring unit at least together with the measurement position and/or measurement time detected by the detection means as a data set via a data interlace to a base unit, and
storing the data set in the base unit, the method further comprising:
communicating a data set from the base unit to a server, and the server comprises at least one stored data structure assigned to the object to be inspected, supplementing the data structure with the data set communicated by the base unit, and the server provides the data structure for an authorized user and/or a user on site,
wherein the data structure is provided as a virtually accessible three-dimensional model of the object to be inspected, and the data structure and the virtual model based thereon are created and then continuously augmented by the server with the data communicated by the base unit concerning an internal structure and/or an internal state of the components of the measuring units, wherein the object is a construction or a moveable object.

13. The method as claimed in claim 12, wherein the data structure is provided in real time.

14. The method as claimed in claim 12, wherein an instruction is communicated by an authorized user via the server.

15. The method as claimed in claim 12, wherein a field of view is detected which encompasses at least the mobile measuring unit and/or the user on site during the determination of the measurement value and surroundings of the measurement position.

16. The method as claimed in claim 12, wherein the measurement position is marked on the object.

17. The method as claimed in claim 12, wherein direct surroundings of the measurement position are captured photographically and/or on film.

18. The method as claimed in claim 12, wherein a measurement or a capture is automatically effected when a predefined measurement position is reached.

* * * * *